United States Patent
Childers et al.

(10) Patent No.: US 6,413,921 B1
(45) Date of Patent: Jul. 2, 2002

(54) ANTIMICROBIAL COMPOSITION CONTAINING PARACHLOROMETAXYLENOL (PCMX)

(75) Inventors: David Childers, Huntington, WV (US); David Jeng, Lisle, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/630,678

(22) Filed: Aug. 1, 2000

(51) Int. Cl.$^7$ .............................. A61K 7/40; C11D 3/00
(52) U.S. Cl. ................. 510/131; 510/132; 510/137; 510/383; 510/386; 510/518
(58) Field of Search ................... 510/130, 131, 510/137, 159, 383, 405, 428, 433, 488; 424/400, 401, 404, 405

(56) References Cited

U.S. PATENT DOCUMENTS

| | | | |
|---|---|---|---|
| 4,632,772 A | 12/1986 | Garabedian et al. | 252/106 |
| 5,114,978 A | 5/1992 | Corti et al. | 514/737 |
| 5,439,681 A | 8/1995 | Khan et al. | 424/400 |
| 5,494,533 A | 2/1996 | Woodin, Jr. et al. | 134/40 |
| 5,635,462 A * | 6/1997 | Fendler et al. | 510/131 |
| 5,681,802 A * | 10/1997 | Fujiwara et al. | 510/130 |
| 6,017,861 A * | 1/2000 | Fujiwara et al. | 510/130 |
| 6,034,043 A * | 3/2000 | Fujiwara et al. | 510/130 |
| 6,071,866 A * | 6/2000 | Fujiwara et al. | 510/130 |
| 6,190,674 B1 * | 2/2001 | Beerse et al. | 424/401 |
| 6,190,675 B1 * | 2/2001 | Beerse et al. | 424/401 |
| 6,214,363 B1 * | 4/2001 | Beerse et al. | 424/404 |

* cited by examiner

*Primary Examiner*—Necholus Ogden
(74) *Attorney, Agent, or Firm*—Andrew G. Rozycki; Donald O. NIckey

(57) ABSTRACT

The present invention provides an antimicrobial composition for disinfection of a skin surface in preparation for surgery. The antimicrobial composition comprises parachlorometaxylenol (PCMX) and an anionic surfactant composition which exhibits both a high degree of antimicrobial efficacy and low skin irritability properties. In a preferred embodiment, the composition comprises an anionic surfactant composition comprising a surfactant having a hydrophobic portion consisting of a linear alkyl and a hydrophilic portion having ethoxylation termination with a sulfonate anionic group, and a sarcosine surfactant. A preferred surfactant composition further comprises a foaming anionic surfactant, such as sodium lauryl sulfate. The antimicrobial composition can be used in skin disinfecting formulations, such as scrub formulations and pre-operative skin disinfecting formulations. In one embodiment, the composition comprises about 3.3% parachlorometaxylenol. The composition can be used as a surgical scrub formulation or in various pre-surgical skin disinfecting products, including sponges, swabs and topical application devices.

21 Claims, No Drawings

ANTIMICROBIAL COMPOSITION CONTAINING PARACHLOROMETAXYLENOL (PCMX)

FIELD OF THE INVENTION

The invention relates to antimicrobial compositions for providing disinfecting treatment and sustained antimicrobial effectiveness to the skin surface with minimized skin irritation. In particular, the invention relates to compositions containing parachlorometaxylenol (PCMX) which are useful in surgical scrub and pre-operative skin disinfecting formulations.

BACKGROUND OF THE INVENTION

Standard surgical procedures require disinfection of skin surfaces of both the surgeon and patient at the surgical site prior to surgery. Effective pre-operative cleansing of skin is critical to reducing the risk of infection to the patient. Surgical scrub and pre-operative skin preparations are therefore important to control the risk of infection.

Microorganisms on the skin can be transient or resident. Transient microorganisms lie on the surface of the skin, whereas resident microorganisms are found at deeper sites in the skin. It is desirable to kill microorganisms on the skin prior to surgery and sustain the antimicrobial activity of the skin surface as effectively as possible through the duration of the surgical procedure.

Effective antiseptic compositions can be produced by combining a surfactant or detergent with an antimicrobial agent. However, many such compositions are unsuitable for contact with human skin, and can cause discomfort and irritation to the skin. The development of formulations containing antimicrobial agents and detergents that provide acceptable antiseptic properties as well as avoid skin irritation has proven difficult, since the effectiveness of the antimicrobial agent is often reduced by the additional ingredients used.

Parachlorometaxylenol (PCMX) has a phenolic chemical structure and is related to compounds such as cresol, carbolic acid, and hexachloroprene. PCMX is a desirable antimicrobial agent and is particularly effective against a wide variety of gram-positive and gram-negative bacteria. PCMX goes by a variety of other names, including chloroxylenol; 4-chloro-3,5 xylenol; 4-chloro-3,5-dimethylphenol; 2-chloro-m-xylenol; 2-chloro-5-hydroxy-m-xylene; 2-chloro-5-hydroxy-m-xylene; 2-chloro-5-hydroxy-1,3-dimethylbenzene; 4-chlor-1-hydroxy-3,5-dimethyl benzene; and 3,5-dimethyl-4-chlorophenol. Antimicrobial formulations containing PCMX as a disinfecting ingredient are well-known in the art and disclosed by Garabedian et al., U.S. Pat. No. 4,632,772; Corti et al., U.S. Pat. No. 5,114,978; Kahn et al., U.S. Pat. No. 5,439,681; and Woodin, Jr. et al., U.S. Pat. No. 5,494,533.

The antimicrobial effectiveness of PCMX is desirable, however, formulations containing PCMX are difficult to prepare due to its incompatibility with many surfactants as well as other types of compounds. The efficacy of PCMX is often compromised by a variety of factors, such as additional ingredients (e.g., surfactants), pH level, and solubility. For example, see Kahn et al., U.S. Pat. No. 5,439,681, which discloses the difficulty of combining surfactants with PCMX while preserving antiseptic efficacy. Dryness and irritation to the skin are also frequently associated with phenolic antimicrobial compounds such as PCMX.

Development of an antimicrobial formulation containing PCMX which demonstrates both a high degree of antimicrobial effectiveness and low skin irritation properties has proven even more difficult. Thus, there exists a need for improved skin disinfecting formulations suitable for surgery containing PCMX.

SUMMARY OF THE INVENTION

The present invention provides an antimicrobial composition useful for preparing and disinfecting skin prior to surgery. In particular, the composition of the invention can be used as a surgical scrub formulation or pre-surgical skin disinfecting formulation. The pre-operative antimicrobial skin composition comprises parachlorometaxylenol (PCMX) as the antimicrobial agent and an anionic surfactant composition comprising a surfactant having a hydrophobic portion consisting of a linear alkyl and a hydrophilic portion having ethoxylation termination with a sulfonate anionic group; and a sarcosine surfactant. Preferably, the anionic surfactant composition further comprises a foaming anionic surfactant, such as sodium lauryl sulfate. It has now been found that antimicrobial compositions containing PCMX and a combination of certain types of anionic surfactants exhibit both a high degree of initial and persistent antimicrobial efficacy, as well as a low degree of skin irritability.

There is further disclosed an antimicrobial composition for disinfection of a skin surface consisting essentially of:

a) parachlorometaxylenol in an amount of about 3.3% by weight;
b) sodium $C_{12-15}$ pareth-15 sulfonate in an amount of about 6.3% by weight;
c) sodium lauroyl sarcosinate in an amount of about 3.0% by weight;
d) sodium lauryl sulfate in an amount of about 1.05% by weight;
e) soy acid in an amount of about 0.3% by weight;
f) propylene glycol in an amount of about 9.0% by weight;
g) PEG-120 methyl glucose dioleate in an amount of about 3.0% by weight;
h) water in an amount of about 72.47% by weight;
i) phenoxyethanol in an amount of about 1.0% by weight;
j) citric acid in an amount of about 0.26% by weight;
k) sodium hydroxide in an amount of about 0.02% by weight; and
l) styrene/PVP co-polymer in an amount of about 0.3% by weight.

The invention also relates to a topical application device containing the antimicrobial composition according to the invention.

The invention further provides for a method of disinfecting skin comprising applying to the surface of the skin to be disinfected an antiseptically effective amount of an antimicrobial composition comprising parachlorometaxylenol; and an anionic surfactant composition comprising a surfactant having a hydrophobic portion consisting of a linear alkyl and a hydrophilic portion having ethoxylation termination with a sulfonate anionic group; and a sarcosine surfactant.

Among the advantages associated with the antimicrobial composition of the invention is that it exhibits the high antimicrobial effectiveness associated with PCMX while also having significantly reduced skin irritability. Another advantage of the invention is that the composition has been formulated to provide a viscous, mild and low odor product without impairing the antimicrobial efficacy of the active ingredient and cleansing properties of the surfactants used in the composition.

DETAILED DESCRIPTION OF THE INVENTION

The antimicrobial composition of the invention comprises a combination of parachlorometaxylenol (PCMX) and additional ingredients including surfactants which when utilized provides the high degree of antiseptic efficacy of PCMX in combination with a low degree of irritation to the skin.

The antimicrobial agent, parachlorometaxylenol, is present in the composition in an antimicrobially effective amount. PCMX can be present in an amount ranging from about 1.0% to about 5.0% by weight. Preferably, PCMX is present in the composition in an amount from about 3.0% to about 4.0% by weight. In one embodiment, PCMX is present in an amount of about 3.3% by weight of the composition. A representative PCMX that can be used in the invention includes NIPACIDE™ PX-R, which is available from Nipa Hardwicke, Inc. of Wilmington, Del.

The composition further comprises a combination of anionic surfactants which function to preserve the antimicrobial activity of PCMX, are compatible with the other surfactants used, and reduce the irritability of the composition. The anionic surfactant composition can collectively comprise between about 5% to about 15% by weight of the composition and includes an anionic surfactant having a hydrophobic portion consisting of a linear alkyl chain and a hydrophilic portion having ethoxylation termination and an sulfonate anionic group; and a sarcosine surfactant. In a preferred embodiment, the anionic surfactant composition further comprises a foaming anionic surfactant, such as sodium lauryl sulfate. The amounts of each surfactant in the surfactant composition can vary slightly, provided the properties contributed by each of the surfactants is maintained in the composition.

A preferred anionic sulfonate surfactant having a hydrophobic portion consisting of a linear alkyl chain and a hydrophilic portion having ethoxylation termination with an anionic sulfonate group is one having a hydrophilic portion consisting of 15 moles of ethoxylation termination and having a hydrophilic lipophilic balance (HLB) of about 15.4. Ethoxylation termination, i.e., the presence of ethoxy moieties as an end functional group on the hydrophilic portion of the compound, enhances the hydrophilic properties of the surfactant. Most preferred as the anionic sulfonate surfactant is sodium $C_{12-15}$ pareth-1 5 sulfonate, which has the chemical formula $H(CH_2)_{12-15}-(OC_2H_4)_{15}-SO_3^-Na^+$ (commercially available as AVANEL™S-150 from BASF Corporation, Mount Olive, N.J.). Sodium $C_{12-15}$ pareth-15 sulfonate possesses a unique chemical structure and pH stability, mildness and anti-irritant properties, as well as an ability to reduce the irritability of other surfactants including sodium lauryl sulfate.

The anionic surfactant composition used in the invention also comprises a surfactant which is compatible with phenolic antimicrobial compounds. Preferred phenolic-compatible surfactants include sarcosine surfactants selected from the group comprising sodium lauroyl sarcosinate, sodium cocoyl sarcosinate, and combinations thereof. It has been found that the sarcosine surfactants are compatible with both other anionic surfactants and phenolic compounds (e.g., PCMX). Most preferred as the sarcosine surfactant is sodium lauroyl sarcosinate (commercially available as HAMPOSYL™ L-30 from W. R. Grace & Co., Nashua, N.H.).

Preferably, the anionic surfactant composition further comprises a foaming anionic surfactant. Suitable foaming anionic surfactants include, but are not limited to, alkyl sulfates and alpha-olefin sulfonates, and combinations thereof. Suitable alkyl sulfates include sodium lauryl sulfate (STEPANOL™ WA-EXTRA available from Stepan Company, Northfield, Ill.) and ammonium lauryl sulfate. Suitable alpha-olefin sulfonates include $C_{14-16}$ olefin sulfonate. Anionic surfactants such as sodium lauryl sulfate exhibit high foaming and lather properties and provide a creamy texture to the overall composition.

The particular combination of PCMX and surfactants in the invention is important to produce the combined properties of antimicrobial efficacy and low irritability of the composition while maintaining chemical compatibility and/or stability between all the ingredients. The composition of the invention not only contains a combination of surfactants compatible with PCMX, but each surfactant is compatible with the others and enhance their respective irritation-reducing functions.

The solvent system used in the antimicrobial composition of the invention must be compatible with the ingredients of the composition. Solvents which can be used include water (deionized) and at least one solvent adapted to solubilize phenolic compounds. Solvents adapted to solubilize phenolic compounds such as PCMX include aliphatic alcohols. Suitable aliphatic alcohol solvents include, but are not limited to, propylene glycol, hexylene glycol, and triethylene glycol.

The composition can also include a pH buffer system. Any pH buffer system which is compatible with the composition ingredients and can stabilize the pH of the composition can be used. Typical pH buffer systems contain an acidulent and an alkalizing agent. Suitable acidulents include, but are not limited to, citric acid, hydrochloric acid, and phosphoric acid. Suitable alkalizing agents include, but are not limited to, sodium hydroxide (e.g., sodium hydroxide NF), and disodium phosphate.

Preferred antimicrobial compositions of the invention further comprise an emollient. Suitable emollients for the invention include, but are not limited to, vegetable fatty acids. Preferred vegetable fatty acids for use in the invention are those with phospholipids containing linoleic acid. For example, soya fatty acid can be used, such as EMERY™ 610 Soya Fatty Acid available from Emery Industries, Inc./Cognis Corporation, Cincinnati, Ohio.

Viscosity enhancers or thickeners can also be included in the composition of the invention, provided they are compatible with the ingredients of the composition. Viscosity enhancers which also function as anti-irritants are preferred. Suitable thickeners include, but are not limited to, polyethylene glycol and polyethylene glycol derivatives. Polyethylene glycol derivatives which can be used include methyl glucoside derivatives, such as PEG-120 methyl glucose dioleate (commercially available as GLUCAMATE™ DOE-120 from Amerchol Corporation, Edison, N.J.), PEG-120 Methyl Glucose Trioleate, PEG-150 distearate, PEG-5M and PEG-14M.

The composition of the invention can further contain other ingredients including, but not limited to, preservatives, opacifiers, foaming agents, emulsifiers, solubilizers, and the like. Preservatives which can be used include those which are typically used in topical cosmetic formulations. For example, phenoxyethanol (e.g., PHENOXYTOL™ Nipa Hardwicke, Inc., Wilmington, Del.) can be used.

When opacifiers are used, any conventional opacifier adapted to remain in solution and render the composition non-transparent can be used. Suitable opacifiers include polymeric opacifiers such as styrene/polyvinylpyrrolidone co-polymers and styrene/acrylic emulsions. Styrene/ polyvinylpyrrolidone co-polymers which can be used include, for example, POLECTRON™ 430 (available from ISP Technologies, Inc., Calvert City, Ky.) can be used. Styrene/acrylic emulsions which can be used include sodium styrene/acrylate/divinyl-benzene co-polymer and ammonium nonoxynol-4 sulfate; sodium stytene/PEG-10 maleate/ nonoxynol-10 maleate/acrylates co-polymer and ammonium nonoxynol-4 sulfate; styrene/acrylamide co-polymer and ammonium nonoxynol-4 sulfate; styrene/acrylates co-polymer and sodium lauryl sulfate and octoxynol-9; sodium styrene/acrylates co-polymer and sodium lauryl sulfate and tridecath-7; sodium methacrylate/styrene co-polymer and sodium lauryl sulfate and tridecath-7 and sodium lauryl diphenyloxide-disulfonate; and sodium styrene/acrylates co-polymer (available from CSA, Inc., Greenville, S.C.).

Variations in the type and amount of additional ingredients are possible provided that the combination thereof does not adversely affect the antimicrobial efficacy and anti-irritation properties of the overall composition.

The process for preparing the antimicrobial composition of the invention generally involves the addition of the ingredients under continuous agitation and under controlled temperature conditions. For example, the preparation of the composition can begin with the combining of PCMX, surfactants, emollient, phenol-compatible solvent (e.g., propylene glycol), and thickener while continuously stirring and warming to a temperature of about 60° C. until the ingredients are dissolved. The temperature can then be cooled to about 45° C. or less. The preservative (e.g., phenoxyethanol) can then be added at this time. Water can then be added as the solvent, followed by the acidulent and alkalizing agents of the pH buffer system, all while maintaining a temperature of about 45° C. or less. Variations in the preparation process are possible.

In general, the antimicrobial composition of the invention is applied topically to the skin in the area on which the antimicrobial treatment is desired during an antiseptic cleansing procedure. The composition can be applied to the skin surface using any suitable device or technique adapted for topical delivery of liquid formulations. In a further embodiment, the antimicrobial composition of the invention can be incorporated into a topical application device. Suitable topical application devices include, but are not limited to, sponges, sponge sticks, scrub brushes, swabs, fluid dispensing devices, and the like.

The antimicrobial composition of the invention exhibits a high degree of both initial and sustained antimicrobial efficacy while at the same time exhibits a reduced degree of skin irritability normally associated with the topical use of compositions containing PCMX as the active antimicrobial agent.

The invention is further illustrated by the following example, none of which should be construed to limit the invention.

EXAMPLE 1

Preparation of PCMX 3.3% (by Weight) Scrub Formulation To a 400 ml beaker fitted with a magnetic stirrer was added 63.0 g of sodium $C_{12-15}$ pareth-15 sulfonate (AVANEL™ 7 S-150 CG, 35% aqueous solution), 35.0 g of sodium lauroyl sarcosinate (HAMPOSYLC™ L-30, 30% aqueous solution), 1.05 g of soya acid (EMERY™ 610 Soya Fatty Acid), 31.5 g propylene glycol, 10.5 g of a viscosity enhancer (GLUCAMATE™ DOE-120), 12.25 g of sodium lauryl sulfate (STEPANOL™ WA-EXTRA, 30% aqueous solution) and 11.55 g of PCMX (NIPICIDE™ PX-R) while the mixture was heated on a hotplate to a temperature of 60° C. under continued mixing until all ingredients were dissolved. The mixture was then cooled to a temperature of at or below about 45° C. 3.5 g of phenoxyethanol (PHENOXYTOL™) was added to the mixture following cooling.

Deionized water was slowly added to the mixture, followed by the buffer system. Initially, 0.875 g citric acid in a 20% by weight aqueous solution was added and dissolved, followed by 0.07 g sodium hydroxide in a 5% by weight aqueous solution, under continuous stirring. While continuously mixing, 2.45 g of opacifier (POLECTRON™ 430, 43% solution) was added along with the remaining water. The pH was adjusted to about 5.44, and the remaining water was added while a temperature of 45° C. or below was maintained.

The resultant antimicrobial composition had the following content:

TABLE 1

Antimicrobial Composition (3/3% PCMX)

| Ingredient | Grams | % by Weight |
| --- | --- | --- |
| Solvent (water) | 178.255 | 50.93 |
| Surfactant (Avanel S-150 CG)* | 63.0 | 18.0 |
| Surfactant (Hamposyl L-30)* | 35.0 | 10.0 |
| Surfactant (Stepanol WA-EXTRA)* | 12.25 | 3.5 |
| Emollient | 1.05 | 0.3 |
| Thickener/anti-irritant | 10.5 | 3.0 |
| PCMX | 11.55 | 3.3 |
| Preservative | 3.5 | 1.0 |
| Acidulent | 0.875 | 0.25 |
| Alkalizing agent | 0.07 | 0.2 |
| Solvent (phenolic-compatible) | 31.5 | 9.0 |
| Opacifier* | 2.45 | 0.7 |
| Total | 350.0 | 100.0 |

*The amount recited for this ingredient is the total amount of the product added, which includes the specific % of active ingredient for such product as recited in the preceding description of the experiment. An ordinarily skilled artisan will appreciate, therefore, that in this and the following Examples which use the cornmercial product source, that 18.0% by weight of the product AVANEL S-150 (35% solution) contains about 6.3% by weight of the active ingredient; 10% by weight HAMPOSYL 1-30 (30% solution) contains about 3.0% by weight active ingredient; 3.5% by weight STEPANOL WA-EXTRA (30% solution) contains about 1.05% by weight active ingredient; and 0.7% by weight POLECTRON 430 (43% solution) contains about 0.3% by weight active ingredient.

EXAMPLE 2

Comparative In Vitro Time Kill Study

Antimicrobial efficacy was evaluated for eight test products. Formulations 1 through 7 were prepared in accordance with the invention and as set forth in Example 1. An eighth composition, hereinafter identified as Formula 8, is the commercially available product known as ULTRADEX™ and is described in Garbedian et al., U.S. Pat. No. 4,632,772, (incorporated herein by reference) containing from 1.5 to 3.75%, preferably 2 to 3.25% PCMX and available from Dexide, Inc., Ft. Worth, Tex. The specific formulation is proprietary and its exact ingredients and proportions are not generally available to the public.

The formulations are summarized in Table 2 below:

TABLE 2

| Ingredient | PCMX Formulations Tested | | | | | | |
| --- | --- | --- | --- | --- | --- | --- | --- |
| | 1 | 2 | 3 | 4 | 5 | 6 | 7 |
| Water | 50.93 | 41.92 | 51.19 | 42.19 | 50.62 | 50.82 | 50.72 |
| Chloroxylenol (PCMX) | 3.30 | 3.75 | 3.30 | 3.75 | 3.30 | 3.30 | 3.30 |
| Sodium $C_{12-15}$ Pareth-15 Sulfonate* | 18.00 | 21.80 | 18.00 | 21.80 | 18.00 | 18.00 | 18.00 |
| Sodium Lauroyl Sarcosinate* | 10.00 | 12.10 | 10.00 | 12.10 | 10.00 | 10.00 | 10.00 |
| Sodium Lauryl Sulfate* | 3.50 | 4.20 | 3.50 | 4.20 | 3.50 | 3.50 | 3.50 |
| Soy Acid | 0.30 | 0.3 | — | — | — | 0.30 | 0.30 |
| Lecithin (50% in propylene glycol) | — | — | — | — | 0.60 | — | — |
| PEG-120 Methyl Glucose Dioleate | 3.00 | 3.00 | 3.00 | 3.00 | 3.00 | 3.00 | 3.00 |
| Phenoxyethanol | 1.00 | 1.00 | 1.00 | 1.00 | 1.00 | 1.00 | 1.00 |
| Citric Acid | 0.25 | 0.31 | 0.29 | 0.34 | 0.26 | 0.26 | 0.26 |
| Sodium Hydroxide | 0.02 | 0.02 | 0.02 | 0.02 | 0.02 | 0.02 | 0.02 |
| Propylene Glycol | 9.00 | 10.90 | 9.00 | 10.90 | 9.00 | 9.00 | 9.00 |
| Styrene/PVP Co-polymer* | 0.70 | 0.70 | 0.70 | 0.70 | 0.70 | 0.70 | 0.70 |
| Disodium EDTA | — | — | — | — | — | 0.10 | 0.20 |
| Total % by weight | 100.00 | 100.00 | 100.00 | 100.00 | 100.00 | 100.00 | 100.00 |

Preparation of Microorganism Strains

Three different microorganism strains (*Escherichia coli* (ATCC 11229), *Staphylococcus aureus* (ATCC 6538) and *Enterococcus faecalis* (ATCC 51575) were used to evaluate antimicrobial properties of these formulations. Inoculi were prepared using standard techniques. Forty-eight hours prior to the study, sterile tubes containing Tryptic Soy Broth were inoculated for each microorganism from stock cultures and incubated for approximately 24 hours at 35° C.±2° C. Approximately 24 hours prior to initiating the study, the broth cultures were inoculated onto the surface of Tryptic Soy Agar plates and incubated for approximately 24 hours at 35° C. 2° C. Challenge suspensions were prepared immediately prior to testing by inoculation of test tubes containing Butterfield's Phosphate Buffer (BBP) solution with the microorganisms from the solid media plates. Suspensions were prepared at concentrations of approximately $1.0 \times 10^9$ CFU/ml as determined by placing loopfuls of microorganisms into a test tube of BBP and comparing turbidity to a standard until approximately $1.0 \times 10^9$ CFU/ml was indicated. The initial population of each microorganism was determined using conventional techniques by making 10-fold dilutions ($10^{-1}$, $10^{-2}$, $10^{-3}$, $10^{-4}$, $10^{-5}$, $10^{-6}$, $10^{-7}$) starting with the first 10-fold dilution ($10^{-1}$), which was prepared by placing 1.0 ml of the challenge suspension into a test tube containing 9.0 ml Butterfield's Phosphate Buffer solution. The remaining 10-fold dilutions were prepared by serial dilution of 0.5 ml aliquots in test tubes containing 4.5 ml Butterfield's Phosphate Buffer solution and mixed using a vortex mixer. Appropriate serial dilutions were prepared from 0.1 ml aliquots and pour plated to produce plated dilutions and incubated.

Neutralization Study

A neutralization study was performed using *S. aureus* (ATCC 6538) prior to testing to ensure that the neutralizing solution employed, Butterfield's Phosphate Buffer solution with the product neutralizers (BBP++) was effective in neutralizing the antimicrobial properties of the test formulations.

Testing Procedure

Formulations 1 through 7 were tested at 99% by volume concentration using two (*Escherichia coli* and *Staphylococcus aureus*) of three microorganisms at exposure times of 1 minute, 3 minutes, and 6 minutes. Formulations 1 through 5 and 8 were also tested at 50% by volume concentration using all three microorganism strains (*Escherichia coli*, *Staphylococcus aureus* and *Enterococcus faecalis*) at exposure times of 15 seconds, 30 seconds, 1 minute and 3 minutes. The microorganism strains are hereinafter referred to as *E. coli*, *S. aureus* and *E. faecalis*.

Aliquots (0.1 ml) of each challenge suspension (containing approximately $1.0 \times 10^9$ CFU/ml of test microorganism) were inoculated into sterile test tubes containing 9.9 ml of test formulation and mixed using a vortex mixer to achieve a 99% by volume concentration of test formulation. Microorganism exposure to the formulation was timed using a calibrated minute/second timer. Formulations 1 through 7 were tested using *E. coli* and *S. aureus*.

Aliquots (0.1 ml) of each challenge suspension (containing approximately $1.0 \times 10^9$ CFU/ml of test microorganism) were inoculated into sterile test tubes containing 5.0 ml of test formulation and 4.9 ml sterile deionized water and mixed using a vortex mixer to achieve 50% by volume concentration of test formulation. Exposure was timed using a calibrated minute/second timer. Formulations 1 through 5 and 8 were tested using *E. coli*, *S. aureus* and *E. faecalis*.

Following each timed exposure to the formulations, 1.0 ml was removed from each tube and placed in a sterile tube containing 9.0 ml Butterfield's Phosphate Buffer solution with product neutralizers (BBP++) and mixed using a vortex mixer. Ten-fold dilutions were made to $10^{-4}$, $10^{-5}$, and $10^{-6}$. A 1.0 ml aliquot of the $10^{-3}$ dilution and 0.1 ml aliquots of the $10^{-3}$, $10^{-4}$, $10^{-5}$ and $10^{-6}$ formulation/microorganism dilutions were pour plated in duplicate to produce plated dilutions and incubated at 35° C.±2° C. for 20.5 hours for *E. faecalis* and for 20.5–29.5 hours for *E. coli* and *S. aureus*.

Data Collection

After incubation, plate colonies were manually counted using a hand tally counter, with 30 to 300 CFU range counts preferentially used. The $Log_{10}$ Average and the CFU/ml of cially available product which contains PCMX in an amount similar to that of the invention. The formulations of the invention exhibited nearly 100.00% antimicrobial efficacy at all concentrations and exposure times.

TABLE 3

| Micro-<br>Organism | Product<br>Concentration<br>(v/v) | Exposure<br>Time | Percent Reduction | | | | | | | |
|---|---|---|---|---|---|---|---|---|---|---|
| | | | 1 | 2 | 3 | 4 | 5 | 6 | 7 | 8 |
| E. faecalis | 50% | 15 sec. | 99.9673 | 99.9598 | 99.9933 | 99.9937 | 99.9927 | | | 47.4074 |
| | 50% | 30 sec. | 99.9994 | 99.9993 | >99.9999 | >99.9999 | 99.9999 | | | 63.8272 |
| | 50% | 1 min. | >99.9999 | >99.9999 | >99.9999 | >99.9999 | >99.9999 | | | 88.8889 |
| | 50% | 3 min. | >99.9999 | >99.9999 | >99.9999 | >99.9999 | 99.9991 | | | 99.8000 |
| E. coli | 50% | 15 sec. | >99.9999 | 99.9993 | >99.9999 | 99.9999 | >99.9999 | | | 27.0936 |
| | 50% | 30 sec. | >99.9999 | >99.9995 | >99.9999 | 99.9999 | >99.9999 | | | 64.0394 |
| | 50% | 1 min. | >99.9999 | >99.9999 | >99.9999 | >99.9999 | 99.9986 | | | 71.8876 |
| | 50% | 3 min. | >99.9999 | >99.9998 | >99.9999 | >99.9999 | >99.9999 | | | >99.9999 |
| | 99% | 1 min. | >99.9999 | >99.9999 | >99.9999 | >99.9999 | >99.9999 | >99.9999 | >99.9999 | |
| | 99% | 3 min. | >99.9999 | >99.9999 | >99.9999 | >99.9999 | >99.9999 | >99.9999 | >99.9999 | |
| | 99% | 6 min. | >99.9999 | >99.9999 | >99.9999 | >99.9999 | >99.9999 | >99.9999 | >99.9999 | |
| S. aureus | 50% | 15 sec. | >99.9999 | >99.9963 | 99.9997 | 99.9998 | 99.9999 | | | 41.6842 |
| | 50% | 30 sec. | >99.9999 | >99.9993 | 99.9998 | >99.9999 | >99.9999 | | | 72.2105 |
| | 50% | 1 min. | >99.9999 | >99.9999 | >99.9999 | >99.9999 | >99.9999 | | | 99.9698 |
| | 50% | 3 min. | >99.9999 | >99.9999 | >99.9999 | >99.9999 | >99.9999 | | | 99.9988 |
| | 99% | 1 min. | >99.9999 | >99.9999 | >99.9999 | >99.9999 | >99.9999 | >99.9999 | >99.9999 | |
| | 99% | 3 min. | >99.9999 | >99.9999 | >99.9999 | >99.9999 | >99.9999 | >99.9999 | >99.9999 | |
| | 99% | 6 min. | >99.9999 | >99.9999 | >99.9999 | >99.9999 | >99.9999 | >99.9999 | >99.9999 | | the average of duplicate plate counts for the for the initial population and post-exposure population was calculated as follows:

$$Log_{10}\ Average = Log_{10}(C_i \times 10^{-D})\ CFU/ml = (C_i \times 10^{-D})$$

where:

$C_i$=2 plate count average and D=dilution factor $Log_{10}$ Reduction for each time exposure was calculated as follows:

$$Log_{10}\ Reduction = IP - P_{EX}$$

where:

IP=$Log_{10}$ of the initial population of challenge microorganism and $P_{EX}$=$Log_{10}$ of average population after exposure to the test formulation.

Percent Reduction was calculated for each time exposure as follows:

$$Percent\ Reduction = \frac{IP(CFU/ml) - P_{EX}(CFU/ml)}{CFU/ml)} \times 100$$

where:

IP=initial population of challenge microorganism (CFU/ml) and $P_{EX}$=average population after exposure to each product (CFU/ml).

Results

The results from the efficacy study for each formulation compared are summarized in Table 3.

As can be seen from the percent reduction data, the formulations of the invention exhibit superior antimicrobial efficacy against the microorganism strains tested as compared to the antimicrobial properties of formulation 8 (ULTRADEX™), which is a leading, currently commer-

EXAMPLE 3

Comparative Evaluation of Hand Scrub Formulations

Three hand scrub formulations containing PCMX were evaluated for their antimicrobial efficacy under actual use conditions. The Study evaluates the effectiveness of an antimicrobial to reduce resident microbial flora on the human hand. The formulations compared were as follows:

TABLE 4

Hand Scrub Formulations
(All amounts are expressed in % by weight of total composition)

| Ingredient | Formula 9<br>3.3% PCMX | Formula 10<br>3.0% PCMX |
|---|---|---|
| Water | 50.93 | 47.70 |
| PCMX | 3.30 | 3.02 |
| Sodium $C_{12-15}$ Pareth-15 Sulfonate* | 18.00 | — |
| Sodium Lauroyl Sarcosinate* | 10.00 | — |
| Sodium Lauryl Sulfate* | 3.50 | 22.00 |
| Soy Acid | 0.30 | — |
| Cocamidopropyl Betaine* | — | 4.00 |
| Povidone | — | 2.50 |
| PEG-120 MethylGlucose Dioleate | 3.00 | — |
| Phenoxyethanol | 1.00 | — |
| Citric Acid | 0.25 | 0.11 |
| Sodium Hydroxide | 0.02 | 0.02 |
| Propylene Glycol | 9.00 | 20.00 |
| Styrene/PVP Co-polymer* | 0.70 | — |
| Tetrasodium EDTA* | 0 | 0.25 |
| Fragrance | — | 0.40 |
| Total | 100.0 | 100.0 |

*The preceding explanation regarding % total and % active ingredient by weight for products likewise applies to the ingredients Cocamidopropyl Betaine (35% solution) and Tetrasodium EDTA (39% solution) used in this experiment.

The 3rd formulation evaluated, identified as Formulation 11, was the comparative formulation ULTRADEX™ NDC17271-408-10 (with PCMX), the commercially available product referred to in the previous Example and disclosed in Garbedian et al., U.S. Pat. No. 4,632,772.

Test Method

The products were compared using a FDA (Food and Drug Administration) developed test method containing guidelines for testing topical antimicrobials for repeated use. A washout period of at least 14 days (during which no topical or systemic antibiotics, medicated lotions or creams, antibacterial soap products, acne drugs, or dandruff shampoos were used), followed by a baseline period and a five-day treatment period (with a series of washes with the experiment and comparative product). Six subjects (male and female) ranging in age from 18 to 65 were used to evaluate each formulation for a total of 18 subjects. Microbiological samples were obtained from the subjects on selected days at various contact times.

During the baseline period, on Day 1 each subject washed their hands and lower two-thirds of the forearms for 30 seconds using non-medicated soap. The hands and forearms were then rinsed with water for 30 seconds. Microbiological samples were taken of the subjects on Day 1, and repeated on days 3 and 5, 5 and 7, or 3 and 7 of the baseline period. Subjects having baseline estimations averaging greater than or equal to $1.5\times10^5$ CFU/hand after the first two or three estimations qualified for the study.

Subjects initiated treatment within four days of the prior baseline period. The subject's hands and lower two-thirds of the arm were scrubbed in accordance with manufacturer's instructions. Following the scrub, the hands were covered with loose-fitting gloves, with 0 time samples taken approximately one minute following the scrub. Additional samples were taken at three hours or six hours, or both.

A total of three samples were taken on Day 2. Scrubbing and sampling procedures were repeated on the second day of the test, with scrubbing performed an additional two times with at least one hour between. On Days 3 and 4, three scrubs were performed with at least one hour between without samples being taken. One scrub and sampling was performed on Day 5.

Bacterial sampling was conducted by adding a 50 ml aliquot of sampling solution to each loose-fitting glove, with the same sampling solution used for baseline and treatment counts. Gloves were then secured to the wrist and massaged for a period of one minute in a uniform manner. The gloves were removed and approximately 20 ml of the sampling solution was aseptically obtained from the glove.

The sampling solution was plated using standard pour plating technique, incubated, and counted. Initial and serial ten-fold dilutions were prepared using Butterfield's Buffered Dilution Water with neutralizers if needed. Duplicate 1.0 ml aliquots of the diluted solutions were plated. Inoculated plates were incubated for 48 ±4 hours at 37°±1° C. The number of CFUs per sample were determined by taking the average counts from the plates within the range of about 30 to about 300 CFUs.

$Log_{10}$ Reduction per CFU count was calculated using the CFU/hand and $Log_{10}$/Hand data for baseline, Day 1, Day 2, and Day 5 for each subject tested.

Results

The results of the antimicrobial efficacy glove test are summarized in Table 5.

TABLE 5

Average $Log_{10}$ Reduction Summary

| Test Day | Contact Time | Average $Log_{10}$ Reduction |
|---|---|---|
| Formulation 9 (3.3% PCMX Scrub Brush) | | |
| Day 1 | 1 min | 0.6423 |
| | 3 hrs. | 0.1793 |
| | 6 hrs. | 0.5694 |
| Day 2 | 1 min. | 1.5475 |
| | 3 hrs. | 0.7786 |
| | 6 hrs. | 0.1454 |
| Day 5 | 1 min. | 1.9626 |
| | 3 hrs. | 1.9338 |
| | 6 hrs. | 1.3984 |
| Formulation 10 (3.0% PCMX Scrub Brush) | | |
| Day 1 | 1 min | 0.8134 |
| | 3 hrs. | 0.8005 |
| | 6 hrs. | 0.0570 |
| Day 2 | 1 min. | 0.6177 |
| | 3 hrs. | 0.4609 |
| | 6 hrs. | 0.0136 |
| Day 5 | 1 min. | 0.7804 |
| | 3 hrs. | 1.0031 |
| | 6 hrs. | −0.1106 |
| Formula 11 (ULTRADEX ™ NDC17271-408-10) | | |
| Day 1 | 1 min | 0.0958 |
| | 3 hrs. | 0.0491 |
| | 6 hrs. | −0.4572 |
| Day 2 | 1 min. | 0.2360 |
| | 3 hrs. | 0.2033 |
| | 6 hrs. | −0.4817 |
| Day 5 | 1 min. | 0.7969 |
| | 3 hrs. | −0.0388 |
| | 6 hrs. | −0.0493 |

As can be seen from the above data, the 3.3% PCMX formulation of the invention exhibited significantly higher initial and sustained $Log_{10}$ Reduction values as compared to the 3.0% PCMX formulation and the ULTRADEX™ product. Accordingly, the composition of the invention has improved initial and sustained antimicrobial efficacy when in actual use.

EXAMPLE 4

Comparative Cumulative Skin Irritation Study

A Cumulative Irritation Patch Test was performed using three PCMX skin formulations. The test is a modified primary irritation assay which detects weak irritants which require multiple applications to effect a skin reaction. The study was conducted in accordance with the method described in Phillips et al., *Toxicology and Applied Pharmacology*, 21, p. 369–382 (1972), incorporated herein by reference.

The test formulations compared were the same as those identified in Example 3, Table 4 as Formula 9 (3.3% PCMX of the invention), Formula 10 (comparative 3.0% PCMX) and Formula 11 (comparative commercial product ULTRADEX™ and as disclosed in Garbedian et al., U.S. Pat. No. 4,632,772). The formulations were applied for twenty-one (21) days under occlusive patches to skin sites on the scapular back of eight (8) human subjects. Daily re-applications of the same test formulations were made on the same test site for 21 days, or until irritation scores of 3+ or greater were observed. The patches were removed twenty-four (24) hours after each application. The test site was carefully rinsed with distilled water, dried, and examined for irritation, scored and re-patched with fresh test material. The following scale was used to score irritation on test sites:

| Irritation Scores: | |
|---|---|
| 0 | no reaction |
| 1+ | mild erythema covering the entire patch area |
| 2+ | erythema and edema |
| 3+ | erythema, edema, vesicles |
| 4+ | erythema, edema, and bullae |
| X | discontinue application |
| T | tape reaction caused movement of product to new site, stops cumulative scoring at site and starts new scoring. |

The Cumulative Irritation Score is the total number of readings for all subjects. Normalized scores were calculated according to the following formula:

Cumulative Irritation Score×number of days×10=Normalized Score

Test formulations were categorized as irritants based on Cumulative Irritation Scores according to the following scheme:

| | |
|---|---|
| 0–20 | no significant irritation |
| 21–60 | slightly irritating |
| 61–135 | moderately irritating |
| 136+ | highly irritating |

The cumulative irritation results are summarized in the following table:

TABLE 6

Cumulative Irritation Results

| Formulation | Total Cumulative Irritation Score | Normalized Value | Irritation Classification |
|---|---|---|---|
| Formulation 9 3.3% PCMX | 26 | 33 | Slightly irritating |
| Formulation 10 3.0% PCMX | 453 | 566 | Highly irritating |
| Formulation 11 ULTRADEX ™ | 30 | 38 | Slightly irritating |

As can be seen from the above results, the 3.3% PCMX formulations prepared in accordance with the invention had a lower total Cumulative Irritation Score when compared to the 3.0% PCMX formulation and the leading commercial product ULTRADEX™ (which contains PCMX). Accordingly, the antimicrobial PCMX formulation of the invention exhibited improved anti-irritation properties over these other products.

Industrial Applicability

The antimicrobial composition of the invention exhibits a high degree of antimicrobial efficacy as well as reduced skin irritation properties and is therefore useful in a variety of pre-surgical skin products routinely employed by surgeons in preparation for surgery. The composition of the invention can be used in surgical scrub formulations and pre-surgical skin disinfecting formulations. The antimicrobial composition of the invention can applied to the skin surface using any suitable topical application method or technique, or it can be used in conjunction with a variety of topical application devices, such as sponges and surgical fluid dispensing devices and the like.

The complete disclosures of all patents, patent applications, and publications are incorporated herein by reference as if each were individually incorporated by reference. The invention has been described with reference to various specific and preferred embodiments and techniques. However, it should be understood that reasonable variations and modifications are possible from the foregoing disclosure without departing from either the spirit or scope of the present invention as defined by the claims.

What is claimed is:

1. An antimicrobial composition for disinfecting a skin surface comprising:
    a) parachlorometaxylenol in an amount of about 3% to about 4% by weight;
    b) an anionic surfactant composition consisting essentially of sodium $C_{12-15}$ pareth-15 sulfonate, sarcosine surfactant, and sodium lauryl sulfate; and
    c) an emollient.

2. The antimicrobial composition of claim 1, wherein parachlorometaxylenol is present in an amount of about 3.3% by weight of the composition.

3. The antimicrobial composition of claim 1, wherein the sarcosine surfactant is selected from the group consisting of sodium lauroyl sarcosinate, sodium cocoyl sarcosinate, and combinations thereof.

4. The antimicrobial composition of claim 3 wherein the sarcosine surfactant is sodium lauroyl sarcosinate.

5. The antimicrobial composition of claim 1 wherein the emollient is a vegetable fatty acid.

6. The antimicrobial composition of claim 5 wherein the vegetable fatty acid contains a phospholipid having linoleic acid.

7. The antimicrobial composition of claim 6 wherein the vegetable fatty acid is soya acid.

8. The antimicrobial composition of claim 1 further comprising a viscosity enhancer.

9. The antimicrobial composition of claim 8 wherein the viscosity enhancer is a polyethylene glycol glucoside.

10. An antimicrobial composition for disinfection of a skin surface consisting essentially of:
    a) parachlorometaxylenol in an amount from about 3% to about 4% by weight;
    b) sodium $C_{12-15}$ pareth-15 sulfonate;
    c) sodium lauroyl sarcosinate;
    d) sodium lauryl sulfate;
    e) an emollient;
    f) a solvent system comprising water and a phenolic-compatible solvent; and
    g) a viscosity enhancer.

11. The antimicrobial composition of claim 10 further comprising an additional ingredient selected from the group consisting of a preservative, a buffer system, an opacifier and combinations thereof.

12. An antimicrobial composition consisting essentially of:
    a) parachlorometaxylenol in an amount of about 3.3% by weight;
    b) sodium C12–15 pareth-15 sulfonate in an amount of about 6.3% by weight;
    c) sodium lauroyl sarcosinate in an amount of about 3.0% by weight;

d) sodium lauryl sulfate in an amount of about 1.05% by weight;
e) soy acid in an amount of about 0.3% by weight;
f) propylene glycol in an amount of about 9.0% by weight;
g) PEG-120 methyl glucose dioleate in an amount of about 3.0% by weight;
h) water in an amount of about 72.47% by weight;
i) phenoxyethanol in an amount of about 1.0% by weight;
j) citric acid in an amount of about 0.26% by weight;
k) sodium hydroxide in an amount of about 0.02% by weight;
l) styrene/PVP co-polymer in an amount of about 0.3% by weight.

13. A surgical scrub formulation comprising the antimicrobial composition of claim 1.

14. A pre-surgical scrub formulation comprising the antimicrobial composition of claim 1.

15. A topical application device comprising the antimicrobial composition of claim 1.

16. The topical application device of claim 15 wherein said device is a sponge, sponge stick, scrub brush, swab or fluid dispensing device.

17. A method of disinfecting skin comprising applying to the skin surface to be disinfected an antiseptically effective amount of an antimicrobial composition comprising:
a) parachlorometaxylenol in an amount of about 3% to about 4% by weight; and
b) an anionic surfactant composition consisting essentially of sodium $C_{12-15}$ pareth-15 sulfonate, sarcosine surfactant, and sodium lauryl sulfate; and
c) an emollient.

18. The method of claim 17 wherein the sarcosine surfactant is selected from the group consisting of sodium lauroyl sarcosinate, sodium cocoyl sarcosinate and combinations thereof.

19. The method of claim 18 wherein the sarcosine surfactant is sodium lauroyl sarcosinate.

20. The method of claim 17 wherein parachlorometaxylenol is present in an amount of about 3.3% by weight.

21. A method of topically disinfecting skin comprising applying to the skin surface to be disinfected a topical application device containing the antimicrobial composition of claim 1.

* * * * *

UNITED STATES PATENT AND TRADEMARK OFFICE
CERTIFICATE OF CORRECTION

PATENT NO. : 6,413,921 B1  
DATED : July 2, 2002  
INVENTOR(S) : Childers, David and Jeng, David It is certified that error appears in the above-identified patent and that said Letters Patent is hereby corrected as shown below:

Column 5,  
Line 64, "HAMPOSYLC" should read -- HAMPOSYL --.

Column 6,  
TABLE 1, line 26, "3/3%" should read -- 3.3% --.  
Line 47, "1-30" should read -- L-30 --.

Column 14,  
Line 64, part b), "C12-15" should read -- $C_{12-15}$ --.

Signed and Sealed this

Fourteenth Day of January, 2003

JAMES E. ROGAN  
*Director of the United States Patent and Trademark Office*